(12) United States Patent
Burkhart

(10) Patent No.: US 7,323,185 B2
(45) Date of Patent: Jan. 29, 2008

(54) METHODS OF INCREASING THE EFFICACY OF PEROXIDES

(76) Inventor: Craig N. Burkhart, 4556 Crossfields Rd., Toledo, OH (US) 43623

( * ) Notice: Subject to any disclaimer, the term of this patent is extended or adjusted under 35 U.S.C. 154(b) by 396 days.

(21) Appl. No.: 10/847,906

(22) Filed: May 18, 2004

(65) Prior Publication Data

US 2004/0208840 A1 Oct. 21, 2004

Related U.S. Application Data

(63) Continuation of application No. 10/091,607, filed on Mar. 6, 2002, now Pat. No. 6,737,070.

(60) Provisional application No. 60/273,787, filed on Mar. 6, 2001.

(51) Int. Cl.
*A61K 8/02* (2006.01)
*A61K 33/40* (2006.01)
*A61K 33/26* (2006.01)

(52) U.S. Cl. ............... 424/401; 424/400; 424/613; 424/646; 514/859; 514/871; 514/946; 514/947

(58) Field of Classification Search ......... 424/400, 424/401, 613, 646; 514/859, 871, 946, 947
See application file for complete search history.

(56) References Cited

U.S. PATENT DOCUMENTS

| 4,895,727 | A | * | 1/1990 | Allen .................. 424/642 |
| 5,446,028 | A | | 8/1995 | Klein et al. |
| 5,767,098 | A | | 6/1998 | Klein et al. |
| 6,013,637 | A | | 1/2000 | Klein et al. |
| 6,737,070 | B1 | * | 5/2004 | Burkhart .................. 424/401 |

OTHER PUBLICATIONS

Warner, Gregory T. and Plosker, Greg L.; "Clindomycin/Benzoyl Peroxide Gel A Review of its Use in the Management of Acne", American Journal of Clinical Dermatologists 2002 3 (5) pp. 351-353.

* cited by examiner

*Primary Examiner*—Shelley A. Dodson
(74) *Attorney, Agent, or Firm*—MacMillan, Sobanski & Todd, LLC

(57) ABSTRACT

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone, for topical use in dermatology. In a specific embodiment, the invention relates to the use of transitional metals such as Cu(1) and ferrous ions to increase the efficacy of peroxides such as benzoyl peroxide. In another embodiment, the invention relates to a method by which a peroxide such as benzoyl peroxide and its activator are added to the skin surface at the same time. In another embodiment, the invention relates to the use of a more soluble form of peroxide such as benzoyl peroxide to increase its efficacy. In another embodiment, the invention relates to the addition of a side chain to a peroxide such as benzoyl peroxide so that it is activated by light. In a further embodiment, the invention relates to the addition of a tertiary amine to a peroxide such as benzoyl peroxide at the time of skin application, to improve the efficacy of the peroxide. In another embodiment, the invention relates to the addition of dapsone or other material to a peroxide such as benzoyl peroxide to improve its efficacy.

20 Claims, No Drawings

METHODS OF INCREASING THE EFFICACY OF PEROXIDES

CROSS-REFERENCE TO RELATED APPLICATION

This application is a continuation of U.S. application Ser. No. 10/091,607 filed Mar. 6, 2002, now U.S. Pat. No. 6,737,070 issued May 18, 2004, which claimed the benefit of U.S. provisional application Ser. No. 60/273,787, filed Mar. 6, 2001.

BACKGROUND OF THE INVENTION

This invention relates in general to methods of treating skin conditions such as acne, and in particular to methods of increasing the efficacy of peroxides such as benzoyl peroxide in the treatment of skin conditions.

The pathophysiology of acne vulgaris, the most common cutaneous disease, is the consequence of the interplay of follicular hyperkeratinization, bacteria in the follicular canal, and sebum production. The exact mechanism triggering the development of the comedone and the stimuli causing the non-inflamed lesion to become provoked are poorly understood. The microbiology of acne vulgaris and its immunologic ramifications constitute a major thrust of present research in the elucidation of the pathogenesis of inflammatory acne. Within the microbial flora of the pilosebaceous unit, P. acnes is the most meaningful organism in acne causation.

The methods of acne therapy are usually grouped into several categories such as keratolytics, antibacterials, sebosuppressives, and hormones. Benzoyl peroxide (BP) is the most widely used topical agent for acne since its introduction in the 1960's. BP is very effective for the treatment of acne because it is antibacterial, functions as a peeling agent, has comedolytic activity, and reduces free fatty acid levels. Concomitant topical treatment of BP and erythromycin is stated to be superior to BP alone. However, no synergistic activity has been found with this combination. Instead, such combination therapies are hypothesized to gain their efficacy by the coupled action of two effective treatments.

SUMMARY OF THE INVENTION

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone, for topical use in dermatology.

In a specific embodiment, the invention relates to the use of transitional metals such as Cu(1) and ferrous ions to increase the efficacy of peroxides such as benzoyl peroxide.

In another embodiment, the invention relates to a method by which a peroxide such as benzoyl peroxide and its activator (or adjunctive agent) are added to the skin surface at the same time (and not days or months before). This ensures that the ingredients are not inactivated or lost strength by being placed together prior to usage.

In another embodiment, the invention relates to the use of a more soluble form of peroxide such as benzoyl peroxide to increase its efficacy.

In another embodiment, the invention relates to the addition of a side chain to a peroxide such as benzoyl peroxide so that it is activated by light.

In a further embodiment, the invention relates to the addition of a tertiary amine to a peroxide such as benzoyl peroxide at the time of skin application, to improve the efficacy of the peroxide. This could include any tertiary amine structure except for an erythromycin structure.

In another embodiment, the invention relates to the addition of dapsone or other material to a peroxide such as benzoyl peroxide to improve its efficacy.

Various advantages of this invention will become apparent to those skilled in the art from the following detailed description of the preferred embodiments.

DETAILED DESCRIPTION OF THE PREFERRED EMBODIMENTS

This invention relates to methods of increasing the efficacy of peroxides such as benzoyl peroxide in the treatment of skin conditions such as acne. In a preferred embodiment, the invention relates to methods of increasing radicals formed by peroxides on/in the skin, more specifically near/in the comedone (but not limited thereto), for topical use in dermatology. The methods use the radicals formed by peroxides such as benzoyl peroxide, optimizing conditions such that the skin/comedone is the only place they are formed as opposed to in a storage container or wherever the benzoyl peroxide happens to be from the time of application to when the benzoyl peroxide breaks down into its radicals or is metabolized).

The methods of the invention may use the principles of photodynamic therapy directed at acne. Instead of forming radicals in cancer cells, the methods form radicals in/by the comedone (skin surface, sebum within P. acnes). Location and timing of formation of radicals is a very important part of the methods.

The methods use the assumption that radicals derived from BP or other peroxides are the most useful in acne therapy (as opposed to reactive oxygen intermediates used in photodynamic therapy).

In a specific embodiment, the invention relates to the use of transitional metals such as Cu(1) and ferrous ions to increase the efficacy of peroxides such as benzoyl peroxide. The use of transitional metals such as Cu(1) and ferrous ions (as alluded to in the text) to increase the efficacy of benzoyl peroxide. It is anticipated that such an addition to benzoyl peroxide would increase the generation of benzoyloxyl radicals.

The transitional metals include all the elements between Group IIA and IIIa in the periodic table. The list includes zinc, cadmium, mercury, scandium, titanium, vanadium, chromium, manganese, yttrium, zirconium, niobium, molybdenum, technetium, ruthenium, rhodium, palladium, silver, lanthanum, hafnium, tantalum, tungsten, rhenium, osmium, iridium, platinum, gold, mercury, actinium, unnilquadium, unnilpentium, unnilhexium, and uniseptium.

A few characteristics of transitional metals include:
most are harder and more brittle with higher melting points, boiling points, and heats of vaporization than the non-transitional metals.
their ions and compounds are usually colored.
they form many complex ions.
most exhibit multiple oxidation states.
many of them are paramagnetic, as are many of their compounds.
many of the metals and associated compounds are effective catalysts.

In another embodiment, the invention relates to a method by which a peroxide such as benzoyl peroxide and its activator (or adjunctive agent) are added to the skin surface at the same time (and not days or months before). An example of such would be a better package system in which the various ingredients that would be added to benzoyl peroxide would be put into a dispenser with two or three chamber (depending upon the number of items combined) to separate the product's ingredients so they do not interact until the instant you apply them to one's acne. This separation would ensure that the ingredients are not inactivated or lost strength by being placed together prior to usage.

Another example of such a system would be benzoyl peroxide (bp) dissolved in a hydrophobic solvent and the activator in a polar solvent. The BP and activator wouldn't meet until applied onto the skin surface. Lipophilic carriers are well known in the art. For an example of the activator in a hydrophilic solvent, both protic and aprotic solvents are included. Protic solvents such as methanol, ethanol, formamide, N-methylformamide, and water, a hydrogen is attached to the electronegative part of the reagent. The hydrogen has a proton-like character and strongly reacts with anionic nucleophiles. Aprotic solvents do not contain positively polarized hydrogens. These include acetone, acetonnitrile, N,N-dimethylformamide, DMSO, hexamaethylphophoric triamide—the aprotic solvents increase the reactivity of nucleophiles in SN2 reactions (the possible mechanism of radical formation by the BP tertiary amine combination).

Retin A micro is an example of a product released by a polymer. The retin A is stored in a small polymer bead. After application of these beads onto the skin, retin A slowly diffuses out of the polymer and into the skin. The invention would have the activator of benzoyl peroxide radical formation contained in a similar polymer. The activator would be slowly released (by diffusion or breakdown of the polymer) into the skin allowing it to react with BP. Alternatively, the BP could be stored in and released from the polymer. Or, both the activator and BP could be released from their own individual polymers to react when the meet (in the environment of the skin/comedone).

In another embodiment, the invention relates to the use of a more soluble form of peroxide such as benzoyl peroxide to increase its efficacy. The use of a more soluble form of benzoyl peroxide. The present-day products actually use benzoyl peroxide in the form of crystals. We are able to solubilize benzoyl peroxide either by altering its hydric solvents, or by adding a side chain to its structure.

In another embodiment, the invention relates to the addition of a side chain to a peroxide such as benzoyl peroxide so that it is activated by light. We could also add a side chain to benzoyl peroxide so that it is activated by light.

In a further embodiment, the invention relates to the addition of a tertiary amine to a peroxide such as benzoyl peroxide at the time of skin application, to improve the efficacy of the peroxide. This could include any tertiary amine structure except for an erythromycin structure. We believe that benzoyl peroxide efficacy can be improved by adding a tertiary amine at the time of skin application. Therefore, we would be including all substances (and chemicals) which have a tertiary amine within the provisional patent, be they antibiotics or whatever. The invention would include all tertiary amine structures, save for the erythromycin structure that is presently used in a commercial product named benzymycin.

Some nonlimiting examples of tertiary amines include Alfuzosin, Alimemazine, Analgesic drug (Reference 97), Atropine, alpha, alpha-bis [3-(N-benzyl-N-methyl-carbamoyl)-piperidino]-p-xylene dihydrobromide, Bupivacaine, cis-trans-Cavinton, Cloperastine, Cyamemeazine, Cyclopentolate, 2-(4,5-dihydro-1H-imidazol-2-yl)-2-propyl-1,2,3, 4-tetrahydropyrrolo]3,2,1-hi[-indole, 1-decyl-3-(N,N-diethylcarbamoyl) piperidine hydrobromide, Diltiazem, Dimethindene, Diperodone, Disopyramide, Disopyamide, semipreparative, Dixyrazine, Doxazosin, Dropropizine, Hydroxychloroquine and metabolites, Ketoconazole, Laudanosine, Marcaine, Medetomidine, Mepivacaine, Mepivacaine (micro column), Meptazinol, Methadon, Nefopam, Nicotine, Omeprazole, Oxybutynin, Oxyphencyclimide, Pheniramine, 3-PPP, Procyclidine, Promethazine, Proxyphylline, Remoxipride, Tetrahydrozoline, Tetramisole, Tetramisole (micro column), Thioridazine ring-sulphoxide, Tolperisone, Trihexyphenidyl, Trimipramine, Tropicamide, Vamicamide, Verapamil, and Vinca alcaloids. The structures and other characteristics of these tertiary amines can be found on the internet at www.chromtech.se/tertiary.htm. The listed amines are all drugs, but the methods of the invention are not limited to just drugs—any tertiary amine would work.

Along with transition metals, tertiary amines potentiate radical formation by BP. A possible mechanism involves reaction of the amine and BP by a $S_N2$ mechanism. The intermediate thus formed thermally decomposes to benzoyloxy radicals and an amine radical cation. The benzoyloxy radicals may further decompose into phenyl radicals. All of these radicals can react with biological molecules possibly causing some biological effect.

In another embodiment, the invention relates to the addition of dapsone to a peroxide such as benzoyl peroxide to improve its efficacy. Heme is a protoporphyrin. P. acnes actually produces protoporphyrins. 5-aminolevulinic acid (ALA) increases protoporphyrin production by P. acnes. ALA is the same stuff used in photodynamic chemotherapy and photodynamic antimicrobial chemotherapy. Methylene blue, toluidine blue O, phthalocyanine, and haematoporphyrin derivative could also be used. Phenothiazinium dyes could also be used. These materials might work by depleting the antioxidant levels in/around the comedone allowing the BP derived radicals to reach the comedone or spread further throughout the comedone.

Viagra (sildenafil) increases NO production by blood vessels (and maybe the skin). It is an example of a molecule inducing the skin to produce a benzoyl peroxide activator.

Testing and Discussion:

Objective: The purpose was to compare radical activity of BP alone and with various antibiotics to determine whether BP and antibiotics may be chemically synergistic.

Methods: Polymerization of tetra ethylene glycol dimethacrylate was used as a test of BP radical activity. Solutions of BP, antibiotics, and BP and antibiotics were made at 3% w/w in tetraethylene glycol dimethacrylate. All of the antibiotics except erythromycin (ERY) were obtained from prescription pills, which were crushed in a crucible. The portion of the pills that disolved in tetraethylene glycol dimethacrylate were used in the experiment. ERY was obtained in powdered form from Benzamycin® acne treatments. Aliquots of ten drops of these solutions were placed in an eight well plastic plate. The samples were heated in an oven that maintained a temperature range between 90 to 100 degrees Celsius. After various amounts of time the samples were taken out of the oven and tested for gel formation. Polymerization of tetraethylene glycol dimethacrylate was detected visually by swirling a spatula in the solutions. Gelling constituted an indicator of BP radical activity.

Results: The results suggest that radical activity increases upon addition of certain antibiotics, such as erythromycin, to a solution of BP. ERY, minocycline (Vectrin®), and levofloxacin (Levaquin®) in combination with BP caused the tetraethylene glycol dimethacrylate to polymerize the fastest. This is assumed to be due to elevated BP radical formation. Agents that did not augment BP radical activity included doxycycline (Monodox®), and trovofloxacin (Trovan®). Upon storage in a dark room at room temperature, the ERY-BP combination gelled within an hour. The Vectrin®-BP, Diflucan®-BP, Trovan®-BP, Monodox®-BP, and Levaquin®-BP combinations did not gel within six hours. Zithromycin® (a prescription drug containing a macrolide similar to ERY) in combination with BP also gelled within an hour when stored in a dark room at room temperature. Furthermore, Zithromycin®-BP and ERY®-BP solutions gelled within an hour when stored in a refrigerator. Zithromycin® has not been tested yet at higher temperatures.

Discussion: BP induces a variety of biological effects. BP can inhibit metabolic cooperation, alter protein synthesis, induce ornithine decarboxylase activity, cause DNA strand breaks, suppress DNA synthesis, and may interfere with mitochondrial respiration. Several of these effects, such as DNA strand breaks, may be caused by BP-derived radicals. Thus, acne treatments that increase the radical activity of BP may be more effective.

Tertiary amines potentiate radical formation by BP. A possible mechanism involves reaction of the amine and BP by a $S_N2$ mechanism. The intermediate thus formed thermally decomposes to benzoyloxy radicals and an amine radical cation. The benzoyloxy radicals may further decompose into phenyl radicals. All of these radicals can react with biological molecules possibly causing some biological effect. Of the antibiotics tested, ERY, doxycycline (Monodox®), minocycline (Vectrin®), levofloxacin (Levaquin®), and trovofloxacin (Trovan®) contain tertiary amines. ERY-BP, Levaquin®-BP, and Vectrin®-BP combinations all behaved as would be expected as they demonstrated faster kinetics for radical formation than BP alone.

Contaminants and solubility may have caused the unexpected results from the Monodox®-BP and Trovan®-BP combinations. The extra chemicals contained in the pills may have dissolved in the tetraethylene glycol dimethacrylate and acted as plastisizers or radical scavengers, thus, hiding any enhanced radical formation by the antibiotic-BP combination. On the other hand, the contaminants may have accelerated the formation of BP-derived radicals. The contaminants may have affected the results for the Levaquin®-BP and Vectrin®-BP combinations as well. Furthermore, some of the antibiotics may not have dissolved in the tetraethylene glycol dimethacrylate, thus, preventing them from being involved in the experiment as only dissolved material was transferred to the plastic plate for testing.

The most impressive result was the speed that the ERY-BP and Zithromycin®-BP solutions gelled at room temperature and below. The speed of reaction between the macrolides and BP insinuates that all the BP in Benzamycin® may be completely depleted by the time a patient picks up his/her prescription to the time it is applied to his/her body. As Benzamycin® is a very effective drug for the treatment of acne, a novel drug may be formed as a product of reactions of BP and ERY with each other and/or other components in Benzamycin® that is very effective against acne. Finding this chemical may result in the discovery of improved acne treatments that do not require BP. As Zithromycin® similarly increased BP radical formation, it is probable that many macrolides mixed with BP are effective drugs for the treatment of acne.

It may be true that the BP is protected from ERY while stored in its container. For example, much of BP is in a less reactive crystalline form while in acne creams, where as it was fully dissolved in these experiments. Upon application to the skin these crystals of BP may dissolve and react with ERY producing radicals. Depending on where these radicals are formed DNA strand breaks, lipid peroxidation, or other effects may occur.

Conclusion: Radical activity of BP in tetraetylene glycol dimethacrylate is increased when tested in consort with several antibiotics, such as the macrolides. We propose that the tertiary amines contained on certain antibiotics are responsible for catalysis of BP radical formation. If increased radical formation correlates with enhanced biological effect, then these data reveal the possibility of biological synergism in mixtures of BP and antibiotics. An understanding of the mechanism of catalysis of BP radical formation by antibiotics may lead to the discovery of improved treatments for acne.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method of topically treating a skin condition comprising applying to the skin a combination of a peroxide and a transitional metal, the transitional metal increasing the efficacy of the peroxide in the treatment of the skin condition, wherein the peroxide and the transitional metal are kept separate prior to their application to the skin and then combined at the time of their application to the skin.

2. A method according to claim 1 wherein the peroxide and the transitional metal are held in separate chambers prior to their application to the skin.

3. A method according to claim 2 wherein the chambers are part of a dispenser for applying the peroxide and the transitional metal to the skin.

4. A method according to claim 1 wherein at least one of the peroxide and the transitional metal is separately contained in a slow release polymer.

5. A method according to claim 1 wherein the peroxide is benzoyl peroxide.

6. A method according to claim 1 wherein the skin condition is acne.

7. A method according to claim 1 wherein the peroxide is benzoyl peroxide and the skin condition is acne.

8. A method according to claim 1 wherein the transitional metal is an ion of copper or iron.

9. A method of topically treating a skin condition comprising applying to the skin a combination of a peroxide and a transitional metal in metal form, the transitional metal increasing the efficacy of the peroxide in the treatment of the skin condition.

10. A method according to claim 9 wherein the peroxide is benzoyl peroxide.

11. A method according to claim 9 wherein the skin condition is acne.

12. A method according to claim 9 wherein the peroxide is benzoyl peroxide and the skin condition is acne.

13. A method according to claim 9 wherein the transitional metal is an ion of copper or iron.

14. A method of topically treating a skin condition comprising applying to the skin a combination of a peroxide and a transitional metal, the transitional metal increasing the efficacy of the peroxide in the treatment of the skin condition, and further increasing the efficacy of the peroxide by at least one of: (a) increasing the solubility or light activatability of the peroxide before its application, and (b) applying a tertiary amine in combination with the peroxide and the transitional metal.

15. A method according to claim 14 wherein the solubility or light activatability of the peroxide is increased by adding a side chain to the peroxide.

16. A method according to claim 14 wherein the solubility of the peroxide is increased by altering its hydric solvent.

17. A method according to claim 14 wherein the peroxide is benzoyl peroxide.

18. A method according to claim 14 wherein the skin condition is acne.

19. A method according to claim 14 wherein the peroxide is benzoyl peroxide and the skin condition is acne.

20. A method according to claim 14 wherein the transitional metal is an ion of copper or iron.

* * * * *